(12) United States Patent
Bloss et al.

(10) Patent No.: US 9,310,231 B2
(45) Date of Patent: Apr. 12, 2016

(54) CHECKING UNIT AND METHOD FOR CALIBRATING A CHECKING UNIT

(75) Inventors: Michael Bloss, Munich (DE); Wolfgang Deckenbach, Schechen (DE); Werner Heimann, Munich (DE); Hans-Peter Ehrl, Wolfratshausen (DE); Erich Kerst, Unterfohring (DE)

(73) Assignee: GIESECKE & DEVRIENT GMBH, Munich (DE)

( * ) Notice: Subject to any disclaimer, the term of this patent is extended or adjusted under 35 U.S.C. 154(b) by 339 days.

(21) Appl. No.: 14/130,053

(22) PCT Filed: Jul. 3, 2012

(86) PCT No.: PCT/EP2012/002796
§ 371 (c)(1),
(2), (4) Date: Dec. 30, 2013

(87) PCT Pub. No.: WO2013/004373
PCT Pub. Date: Jan. 10, 2013

(65) Prior Publication Data
US 2014/0130568 A1   May 15, 2014

(30) Foreign Application Priority Data

Jul. 4, 2011 (DE) .......................... 10 2011 106 523

(51) Int. Cl.
*G01N 33/00* (2006.01)
*G01D 18/00* (2006.01)
(Continued)

(52) U.S. Cl.
CPC .................. *G01D 18/00* (2013.01); *G01N 1/00* (2013.01); *G01N 21/8914* (2013.01);
(Continued)

(58) Field of Classification Search
CPC .... G01B 11/0691; G01B 13/22; G01B 21/30; G01B 2210/42; G01B 2210/44; G01D 18/00; G01N 1/00; G01N 33/346; G01N 21/57; G01N 21/86; G01N 21/89; G01N 21/8914; G01N 21/91; G01N 21/93; G01N 2021/8663; G01N 2021/8917; G01N 33/367; G01N 37/00; G07D 7/00; G07D 7/168

See application file for complete search history.

(56) References Cited

U.S. PATENT DOCUMENTS 3,834,519 A * 9/1974 Kitazawa ............. B65G 47/244
                                                   198/381
4,761,579 A * 8/1988 Delassus ................ H02N 15/00
                                                   219/648

(Continued)

FOREIGN PATENT DOCUMENTS

DE            4439972 A1      5/1996
DE       102004035494 A1      2/2006
(Continued)

OTHER PUBLICATIONS

German Search Report From Corresponding German Application No. 102011106523.0, dated Jun. 25, 2012.
(Continued)

*Primary Examiner* — David A Rogers
(74) *Attorney, Agent, or Firm* — Workman Nydegger (57) ABSTRACT

The invention relates to a checking unit for checking a material web and to a calibrating method for the checking unit. The checking unit is equipped with drive means for transporting the calibration medium past the checking unit in order to detect a multiplicity of measurement values of the calibration medium. The drive means are arranged in the housing of the checking unit in order for the drive means to be protected from moisture or contaminants from the environment. To obtain a transporting of the calibration medium past the checking unit in spite of the arrangement of the drive means in the housing, drive means are employed that are configured for a contactless interaction with the calibration medium and can transport the calibration medium past the checking unit contactlessly. For this purpose there is preferably used a magnetic interaction between the drive means and the calibration medium.

20 Claims, 4 Drawing Sheets

(51) Int. Cl.
*G01N 33/34* (2006.01)
*G01N 33/36* (2006.01)
*G01N 21/89* (2006.01)
*G01N 21/93* (2006.01)
*G01N 1/00* (2006.01)
*G01N 37/00* (2006.01)
*G01N 21/86* (2006.01)
*G01N 21/91* (2006.01)

(52) U.S. Cl.
CPC ............. *G01N 21/93* (2013.01); *G01N 33/346* (2013.01); *G01N 33/367* (2013.01); *G01N 37/00* (2013.01); *G01N 21/86* (2013.01); *G01N 21/91* (2013.01); *G01N 2021/8663* (2013.01); *G01N 2021/8917* (2013.01)

(56) References Cited

U.S. PATENT DOCUMENTS

| | | | | |
|---|---|---|---|---|
| 5,327,082 A * | 7/1994 | Gabura | ........... | G01B 7/14 250/227.11 |
| 5,991,046 A | 11/1999 | Shakespeare et al. | | |
| 6,040,901 A * | 3/2000 | Stapfer | ........... | G07D 7/00 356/71 |
| 6,044,952 A * | 4/2000 | Haggerty | ........... | G07D 7/12 194/207 |
| 7,146,279 B2 * | 12/2006 | Typpoe | ........... | D21G 9/0009 356/429 |
| 7,593,106 B2 * | 9/2009 | Hellstrom | ........... | G01N 21/57 356/429 |
| 7,737,417 B2 * | 6/2010 | Giering | ........... | G07D 7/122 250/458.1 |
| 8,266,965 B2 * | 9/2012 | Schoen | ........... | B65H 7/125 271/258.01 |
| 8,695,397 B2 * | 4/2014 | Sacquard | ........... | G07D 7/168 250/252.1 |
| 2002/0185615 A1 * | 12/2002 | Giering | ........... | G07D 7/122 250/556 |
| 2003/0066200 A1 * | 4/2003 | Hellstrom | ........... | G01B 21/08 33/501.02 |
| 2004/0129893 A1 * | 7/2004 | Usami | ........... | G07D 7/122 250/461.1 |
| 2004/0178044 A1 * | 9/2004 | Mori | ........... | G07D 7/121 194/206 |
| 2004/0200978 A1 * | 10/2004 | Kamijo | ........... | G01N 21/643 250/458.1 |
| 2005/0189703 A1 * | 9/2005 | Okazaki | ........... | B65G 57/04 271/207 |
| 2006/0063039 A1 * | 3/2006 | Yamaguchi | ........... | G11B 5/855 428/826 |
| 2008/0135780 A1 | 6/2008 | Giering et al. | | |
| 2009/0056412 A1 * | 3/2009 | Graeffe | ........... | D21G 9/0009 73/1.81 |
| 2009/0132195 A1 * | 5/2009 | Holl | ........... | G07D 7/00 702/104 |
| 2010/0231897 A1 | 9/2010 | Hofeldt et al. | | |
| 2013/0277122 A1 * | 10/2013 | Ischdonat | ........... | G01G 17/02 177/1 |
| 2014/0284864 A1 * | 9/2014 | Miyashita | ........... | B07C 3/18 270/58.04 |

FOREIGN PATENT DOCUMENTS

DE 102007038754 A1 2/2009
EP 0195168 A1 9/1986

OTHER PUBLICATIONS

International Search Report corresponding with International PCT Application No. PCT/EP2012/002796, mailed Sep. 4, 2012.

* cited by examiner

CHECKING UNIT AND METHOD FOR CALIBRATING A CHECKING UNIT

BACKGROUND

This invention relates to a checking unit for checking a material web and to a method for calibrating the checking unit.

SUMMARY

Upon the manufacture of a material web, such as e.g. a fibrous material web, the material web is transported through the material web's various production sections with the aid of a transport system. For checking the material web during its manufacture, checking units are used which are installed along a transport path of the material web. While the material web is being transported past the firmly installed checking unit with the aid of a transport system, the checking unit detects measurement values of the material web in order to check one or several certain properties of the material web.

For calibrating a checking unit which is arranged along the transport path of a material web and used for checking a material web upon its manufacture, a calibration medium is usually brought into the measuring plane of the checking unit in order to detect a calibration measurement value of the calibration medium with the checking unit. The calibration medium is for this purpose placed manually against the checking unit—during an interruption of the material web check—so that the calibration medium is brought into the measuring plane of the checking unit temporarily, instead of the material web. The calibration medium has associated therewith a certain target value which the checking unit ideally detects upon a measurement of the calibration medium. Upon calibration the deviation of the actual measurement value from this target value is ascertained. When calibration has been done, the checking unit is so adjusted that the measurement value of the checking unit corresponds to the target value belonging to the calibration medium.

The calibration medium usually has a certain measurement portion in which the calibration measurement value is detected. The target value that the checking unit is to detect within the measurement portion is usually printed on the calibration medium outside the measurement portion. The person carrying out the calibration reads this target value and inputs it to the checking unit manually.

It is disadvantageous in this calibrating method that the calibration measurement value that the checking unit detects is not exactly defined and hardly reproducible. This is because the detection site within the measurement portion of the calibration medium on which the checking unit detects the calibration measurement value is subject to fluctuations in all three spatial directions due to the manual insertion and the mechanical tolerances of the calibration medium. Moreover, the manual insertion of the calibration medium involves the risk of a faulty calibration due to an inexact or false insertion of the calibration medium by the person placing the calibration medium against the checking unit.

An object of the present invention is to state a checking unit and a calibrating method for the checking unit that allows a more exact calibration.

This object is achieved by the subject matter of the independent claims. Claims dependent thereon state advantageous developments and configurations of the invention.

The checking unit is configured for checking a material web and has for this purpose a corresponding operating mode in which the checking unit can check a material web for certain properties. For checking the material web, the checking unit detects several measurement values of the material web transported past the checking unit. Depending on the application, there are checked for example optical, electrical, mechanical or magnetic properties of the material web, e.g. in order to carry out an inspection of a production step for the material web. The checking unit can also be used after manufacture, e.g. for a quality check of the material web. Moreover, the checking unit has a further operating mode in which a calibration of the checking unit can be carried out. In the operating mode set up for calibrating the checking unit, calibration measurement values can be sensed by the checking unit detecting measurement values of a calibration medium which is associated with the checking unit. For this purpose, a multiplicity of calibration measurement values are detected when the calibration medium is being transported past the checking unit for calibration. The operating modes are e.g. programmed in a control device of the checking unit.

The checking unit has a housing which receives measurement elements which are configured both for detecting measurement values of the material web and for detecting calibration measurement values of the calibration medium provided for calibrating the checking unit. The housing of the checking unit moreover has arranged therein drive means which are configured for transporting the calibration medium, which is provided for contactless transporting past the checking unit, past the checking unit through a contactless interaction with the calibration medium.

While in previous calibration the calibration medium was brought into the measuring plane of the checking unit statically and hence only a single calibration measurement value of the calibration medium was detectable, according to the invention the calibration medium is transported past the checking unit for calibration. Through such transporting past it is achieved that not only one, but a multiplicity of calibration measurement values of the calibration medium can be detected at a multiplicity of positions along the calibration medium upon calibration. Due to the multiplicity of calibration measurement values, a greater exactness of the calibration can be obtained than is possible with a single calibration measurement value that is subject to unavoidable fluctuations. From the multiplicity of calibration measurement values there can be established a resulting calibration measurement value that is subject to only small fluctuations. For example, the fluctuations of individual calibration measurement values can be eliminated by forming the average value of the multiplicity of calibration measurement values. This makes a more exact calibration of the checking unit possible.

The calibration medium is not transported past the checking unit through the transport system that is employed for transporting the material web past, however, but rather the checking unit according to the invention provides an independent possibility of transport for the calibration medium through its drive means. The calibration medium is transported past the checking unit through the drive means of the checking unit. However, the drive means of the checking unit are not simply provided through additional components, e.g. through transport components that are arranged outside the checking unit and independently of the checking unit, but rather the drive means are integrated into the checking unit itself. If additional transport components for the calibration medium were employed, they would have to be installed relative to the checking unit and adjusted thereto to be able to carry out a sufficiently exact calibration of the checking unit. Through the integration of the drive means into the checking unit it is achieved that the calibration can be carried out more simply, because it is no longer necessary to adjust any additional transport components relative to the checking unit.

The drive means for transporting the calibration medium past are thus not arranged outside the checking unit, e.g. by being fastened to the housing of the checking unit, but rather the drive means are contained within the housing of the checking unit. Thus, it is achieved that the drive means are protected from influences from the environment in which the checking unit is to be used for checking the material web. Because the drive means are arranged in the same housing as the measurement elements of the checking unit, a compact structure of the checking unit is obtained. In the case of magnetic drive means, the housing of the checking unit is non-magnetic.

In the production environment of a material web, external influences can occur, e.g. through moisture or contamination, which could impair the function of the drive means. Through an encapsulation of the drive means into the housing of the checking unit the drive means are protected from moisture or contaminants from this environment, such as e.g. from soiling, dust, liquid, water, whose contact with the drive means is to be avoided. The housing of the checking unit is for this purpose sealed so as to be e.g. splash water proof in order to avoid a penetration of liquids from the environment into the housing.

To obtain a transporting of the calibration medium past the checking unit in spite of the arrangement of the drive means in the housing, drive means are employed that are configured for a contactless interaction with the calibration medium and can transport the calibration medium past the checking unit contactlessly. For this purpose there is preferably used a magnetic interaction between the drive means and the calibration medium. The driving power required for transporting the calibration medium past is produced by a contactless interaction of the calibration medium with the drive means of the checking unit. The drive means are for this purpose arranged within the housing of the checking unit directly adjacent to that side of the checking unit that faces the material web to be transported past or the calibration medium to be transported past.

The drive means arranged in the housing of the checking unit have e.g. several magnets. These magnets can be permanent magnets or also electromagnets. The magnets are so arranged that a calibration medium likewise having magnetic elements can be transported past the checking unit with the aid of the magnets of the drive means. The transporting past is obtained through a magnetic interaction between the magnets of the drive means, which are arranged within the housing of the checking unit, and the magnetic elements of the calibration medium (arranged outside the checking unit). The drive means are moved for transporting the calibration medium past. The motion of the drive means causes the magnets of the drive means to be moved such that a calibration medium that has magnetic elements and has been brought into a capture region of the drive means is capturable through the interaction with the moved magnets of the drive means and is transportable past the checking unit. The arrangement of the magnets of the drive means is coordinated with the arrangement of the magnetic elements on the calibration medium such that the calibration medium, when the magnets of the drive means are moved, is transportable past the checking unit in synchronism with a motion of the magnets. Alternatively, it is also possible not to move the drive means but rather to employ static drive means, e.g. fixed-position electromagnets, which are arranged within the housing of the checking unit along the transport direction of the calibration medium and which are energized with a phase shift in order to transport the calibration medium past the checking unit through magnetic interaction.

Through the arrangement of the magnets of the drive means in the housing of the checking unit it is achieved that the calibration medium is transportable past the checking unit in a spatially defined manner and that the lateral position of the calibration medium is reproducible. Thus, reproducible detection sites on the calibration medium and a reproducible calibration are guaranteed.

The magnets of the drive means and the magnetic elements of the calibration medium are preferably so mutually coordinated that an attractive interaction between the magnets of the drive means and the magnetic elements of the calibration medium is produced during the transporting past as continuously as possible, but at least during the detecting of the measurement values of the calibration medium. The magnets of the drive means are so arranged in the checking unit and so chosen in their magnetic field strength that a continuous lateral guidance of the calibration medium is obtained upon the detecting of the measurement values of the calibration medium. But the attractive interaction also leads to an attraction of the calibration medium to the checking unit. To counteract this attraction there can be provided at least one guide element which exerts an opposing force on the calibration medium, so that the calibration medium is transported past the checking unit at a fixed distance therefrom. The guide element is formed e.g. by a non-magnetic guide plate which is arranged as a spacer on the side of the checking unit facing the calibration medium to be transported past, so that it lies between the checking unit and the calibration medium transported past. The guide plate can for this purpose be fastened to this side of the housing of the checking unit.

In a preferred exemplary embodiment, the checking unit has at least two of the drive means which are respectively configured for a contactless interaction with the calibration medium and which are arranged mutually offset transversely to the transport direction of the calibration medium. Moreover, these drive means are preferably so configured and arranged that they can interact with the calibration medium in mutual synchronism. For example, the magnets of these drive means are movable in mutual synchronism. In particular, the mutually offset drive means can be arranged parallel to each other and be configured in like manner. For example, two or several drive wheels are thus mounted on the same axle and their phase relationship so chosen that their magnets are mounted congruently with each other. Through the employment of at least two drive means offset transversely to the transport direction it is achieved that the transport position and transport direction of the calibration medium is very well defined and a completely straight motion of the calibration medium is guaranteed. Further, this increases the lateral stability of the transporting past, which in particular facilitates the onset of transport of the calibration medium brought into the capture region of the drive means.

The magnets of the drive means are in particular so arranged that the magnetic poles of the mutually adjacent magnets are alternately oriented opposite to each other, so that the motion of the magnets of the drive means enables the force of a magnetic north pole and of a magnetic south pole to be alternately provided in the capture region of the drive means. In the case of two or several drive means running parallel to each other, it is thereby avoided that the calibration medium is transported past in an oblique position of the calibration medium if the calibration medium, which is also equipped with alternately poled magnets, has been inadvertently brought into the capture region of the drive means obliquely. With like polarity of the mutually adjacent magnets (in calibration medium as well as drive means) an oblique transporting past can easily occur, however, when the calibration medium is inserted so obliquely that it is captured by magnets of the two drive means which are mutually offset along the transport direction.

The drive means have for example at least one drive wheel, with the magnets of the drive means being movable through a rotation of the drive wheel around its rotational axis. The magnets can for this purpose be fastened directly to the drive wheel or to a carrier element to which the magnets are fastened and which is moved through the rotation of the drive wheel. The carrier element is e.g. a belt, in particular toothed belt, running around the drive wheel, or a chain running around the drive wheel.

The drive means, in particular the one or several drive wheels, preferably have a magnetic or magnetizable body to which the magnets of the drive means are fastened. This increases the magnetic flux between at least two of the magnets of the drive means whose magnetic poles are oriented radially opposite to each other. In comparison to a single magnet or to fastening the magnets to a non-magnetic body, this obtains a greater magnetic force of the magnets, so that the magnetic interaction is possible over a greater distance. Thus, a secure and defined transporting past of the calibration medium is enabled even when there is a relatively great distance between the drive means and the calibration medium. The magnetic or magnetizable body is formed e.g. by a magnetic/magnetizable drive wheel or a magnetic/magnetizable carrier element, in particular a magnetic/magnetizable belt or a magnetic/magnetizable chain.

In some exemplary embodiments there is employed at least one drive wheel along whose circumference the magnets are arranged such that the magnetic field lines of the respective magnet point radially outward with regard to the rotational axis of the drive wheel. For example, in each case exactly one of the magnetic poles of the respective magnet thus points radially outward with regard to a rotational axis of the drive wheel. Preferably there are arranged along the circumference of the drive wheel several magnets whose magnetic north poles point radially outward and several magnets whose magnetic south poles point radially outward. In this case, adjacent magnets are preferably arranged along the circumference of the drive wheel such that the magnetic north pole and the magnetic south pole are alternately oriented radially outward. Alternatively, all the magnets of a drive wheel can also be oriented with their north poles radially outward or all with their south poles radially outward. To obtain an attractive interaction continuously, the magnets of the calibration medium would in the first case be arranged such that all the magnetic south poles point to the drive wheel, and in the second case such that all the magnetic north poles point to the drive wheel.

For example, the rotational axis of the at least one drive wheel is oriented parallel to the transport plane of the calibration medium in which the calibration medium is transported past the checking unit for calibration, and oriented perpendicularly to the transport direction of the calibration medium. But the rotational axis of the at least one drive wheel can also be oriented perpendicularly to the transport plane of the calibration medium. In other exemplary embodiments, the drive means has at least two drive wheels and a carrier element to which the magnets are fastened, the magnets of the drive means being arranged along the carrier element on the side of the carrier element facing away from the drive wheels.

The invention also relates to an arrangement comprising two checking units which oppose each other with regard to the transport path of the material web or of the calibration medium. Preferably, only one of the opposing checking units is equipped with a drive means according to the invention, and the checking unit opposing it is not. In comparison to equipping both checking units with drive means for the calibration medium, this is advantageous because it is then not necessary to mutually coordinate several drive means, e.g. in terms of the phase relationship of the magnets. Moreover, it can thereby be avoided that the calibration medium is inadvertently inserted in the reverse position.

For calibration, the checking unit is removed (temporarily) from the material web, and the checking unit shifted to the calibration operating mode. In this operating mode the motion of the drive means of the checking unit is started. Subsequently the calibration medium is (e.g. manually) arranged on the side of the checking unit intended for sensing measurement values and brought there into the capture region of the drive means where the contactless interaction of the drive means can be effected, e.g. their magnetic force is available. Through the contactless interaction with the drive means of the checking unit, the calibration medium is subsequently transported past the checking unit along the transport direction, in particular through a contactless magnetic interaction. While the calibration medium is being transported past, the checking unit detects with the aid of its measurement elements a multiplicity of calibration measurement values at different positions within a measurement portion of the calibration medium. The multiplicity of detected measurement values are subsequently employed for calibrating the checking unit.

Preferably, the calibration medium is only brought into the capture region of the drive means after the motion of the drive means has been started. This makes it easier for the calibration medium to be manually brought into the capture region of the drive means in comparison to the calibration medium being brought in when the drive means is at rest. For in the case of an alternate opposite polarity of the magnets of the drive means there could arise, when the drive means is at rest, a repulsion position in which the magnets of the drive means and those of the calibration medium to be brought in repel each other. When the drive means is moved, however, the repulsion position and attraction position alternate due to the alternate magnetic polarity. When the calibration medium is brought in manually there is hence obtained in any case a position of the magnets of the drive means that exerts an attractive force on the calibration medium. Further, this enables the calibration medium to be brought in more favorably in ergonomic terms. For when the force of the moved drive means already acts on the calibration medium when the calibration medium is being brought in manually, the operating person can perceive it when bringing in the calibration medium and is thus given direct feedback that the calibration medium has reached the capture region of the drive means.

The calibration medium is configured for bring transportable past the checking unit through a contactless interaction with the drive means, in particular through the motion of the drive means. For this purpose, the calibration medium preferably has magnetic elements that are coordinated with the magnets of the drive means such that the calibration medium can be transported past the checking unit through a magnetic interaction with the drive means. The calibration medium can thus, when the magnets of the drive means are moved, be transported past the checking unit in synchronism with a motion of the magnets of the drive means.

To avoid a false insertion of the calibration medium, the calibration medium is preferably provided with magnetic elements only on one side. Hence, the calibration medium can also be captured by the drive means and transported only in the right position. The magnetic elements of the calibration medium can be permanent magnets or magnetizable constituents of the calibration medium, e.g. one or several ferromagnetic regions.

The calibration medium preferably has a measurement portion in which a multiplicity of measurement values are detected while the calibration medium is being transported past the checking unit. The measurement portion is so configured that there can be established from the measurement values of this measurement portion both a multiplicity of calibration measurement values and at least the target value required for calibrating the checking unit. It is thus achieved that the measurement elements of the checking unit simultaneously detect the multiplicity of calibration measurement values from which a resulting measurement value of the calibration medium is established, and the target value which the checking unit ideally detects and to which the checking unit is adjusted after calibration. The hitherto necessary manual input of the target value read from the calibration medium is hence no longer necessary. That the measurement portion delivers both information items, the target value and the calibration measurement values, is advantageous compared with a previous calibration medium wherein a conventional optical bar code is simply applied to the calibration medium separately from the calibration sample. For an additional bar code, e.g. one affixed beside the measurement portion, is normally not detectable by the measurement elements of the checking unit, in particular upon a non-optical check or when the optical resolution of the checking unit is deficient. For reading an additional bar code, a bar code reader would hence have to be specially provided on or in the checking unit. This is not necessary with the measurement portion that delivers both, the target value and the calibration measurement values.

For example, the measurement portion of the calibration medium has present therein a calibration sample and a bar code superimposed on the calibration sample and representing at least one target value required for calibrating the checking unit, to which the checking unit is to be adjusted. The bar code is arranged over the calibration sample such that the calibration sample is covered by stripe elements of the bar code in certain portions. During the transporting past, the measurement portion is scanned (stepwise or continuously) through detection of the measurement values. The measurement values detected in the interstices between the stripe elements of the bar code are employed as calibration measurement values, and the target value required for calibration is established from the sequence of the stripe elements of the bar code. From the calibration measurement values at least one resulting measurement value of the checking unit is formed, e.g. by calculating the average value of the multiplicity of measurement values. The bar code is e.g. an optical bar code, a magnetic bar code or a many-width bar code, depending on the measurement principle of the checking unit.

The checking unit preferably also has an operating mode in which the checking unit is utilized—off-line, as it were—as a laboratory device, so that material samples of the material web can also be detected outside the production environment of the material web. The checking unit enables through its drive means that a material sample—instead of the calibration medium—can be checked, if it is fastened to a sample carrier configured therefor. The sample carrier is thus configured analogously to the above-described calibration medium and equipped e.g. with corresponding magnets.

To use the checking unit for checking the material web sample, the following steps are carried out:

fastening the material web sample in a measurement portion of a sample carrier, arranging the sample carrier on a side of the checking unit intended for sensing measurement values such that the sample carrier reaches the capture region of the drive means of the checking unit (that were previously set in motion, where applicable), transporting the sample carrier past the checking unit along the transport direction with the aid of the drive means, detecting a multiplicity of measurement values at different positions within a measurement portion of the material web sample with the aid of the measurement elements of the checking unit while the sample carrier is being transported past the checking unit, employing the detected measurement values for checking the material web sample.

BRIEF DESCRIPTION OF THE DRAWINGS

Hereinafter the invention will be explained by way of example with reference to the following figures. There are shown:

FIG. 1 an arrangement comprising two opposing checking units for checking a material web, FIG. 2 a calibration sample (FIG. 2a), a calibration medium (FIG. 2b) and two of the magnets with which the calibration medium is equipped (FIG. 2c), FIG. 3 a side view of two opposing checking units and a calibration medium transported through therebetween (FIG. 3a) and a plan view of the lower checking unit (FIG. 3b), FIG. 4 a first exemplary embodiment for drive means for transporting the calibration medium past, FIG. 5 a second exemplary embodiment for drive means for transporting the calibration medium past, FIG. 6 a third exemplary embodiment for drive means for transporting the calibration medium past.

DETAILED DESCRIPTION OF VARIOUS EMBODIMENTS

While the material web is being transported past the checking unit according to the invention, the checking unit detects measurement values of the material web in order to infer properties of the material web from these measurement values. The properties can be e.g. optical remission, transmission, luminescence or magnetic properties, e.g. of a magnetic printed image or of a security thread, or mechanical properties, e.g. the thickness of the material web or its surface condition, etc. In particular, the checking unit according to the invention is configured for testing luminescent properties of a material web upon whose manufacture luminescent substances are applied to the material web or incorporated into the material web. For example, the checking unit is employed for checking a paper web in a paper machine and is thus arranged within the paper machine such that it is usable for checking optical properties of the paper web during the manufacture of the paper web when the paper web is being transported through the paper machine. For calibration, the checking unit, which is normally installed along a transport path of the material web, is usually removed temporarily from the measurement position for checking the material web and calibrated in this removed position. Alternatively, the checking unit can be arranged during calibration in that position along the transport path of the material web in which the checking unit also checks the material web, e.g. when production of the material web is interrupted.

Figure 1:
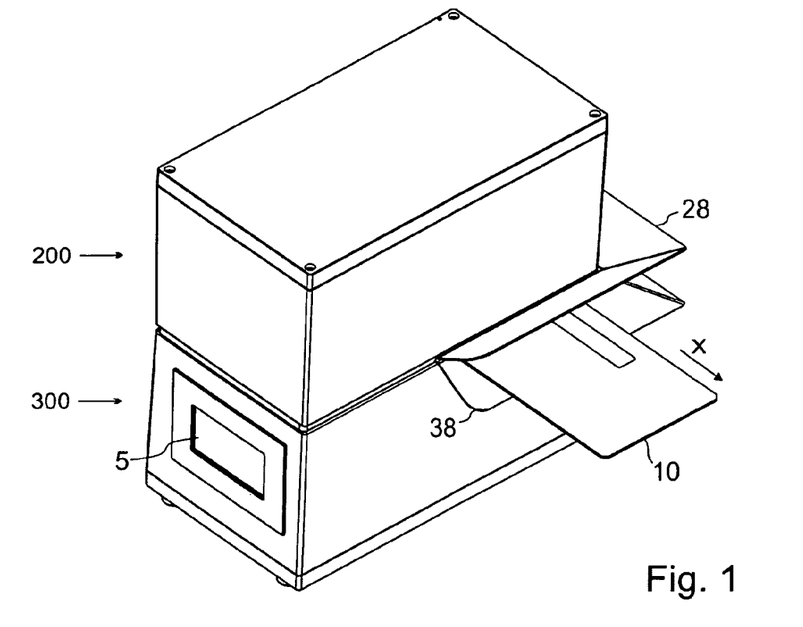

FIG. 1 shows an arrangement comprising two mutually opposing checking units 200, 300 for checking a material web, between which a calibration medium 10 is transported through along the transport direction x in order for it to be scanned on both sides. For checking a material web, the material web is transported through between the two checking units 200, 300, instead of the calibration medium 10. On their front sides the two checking units are equipped with guide plates 28, 38 which guide the material web or the calibration medium 10 in their transport plane T through between the checking units. The two checking units 200, 300 are electronically interconnected (not shown) in order to exchange control commands or data. The checking unit 300 has a display screen 5 for outputting the results of the material web check. Instead of the arrangement from FIG. 1 it is equally possible to employ only the checking unit 300, e.g. for a one-sided check of the material web.

Figures 2A, 2B:
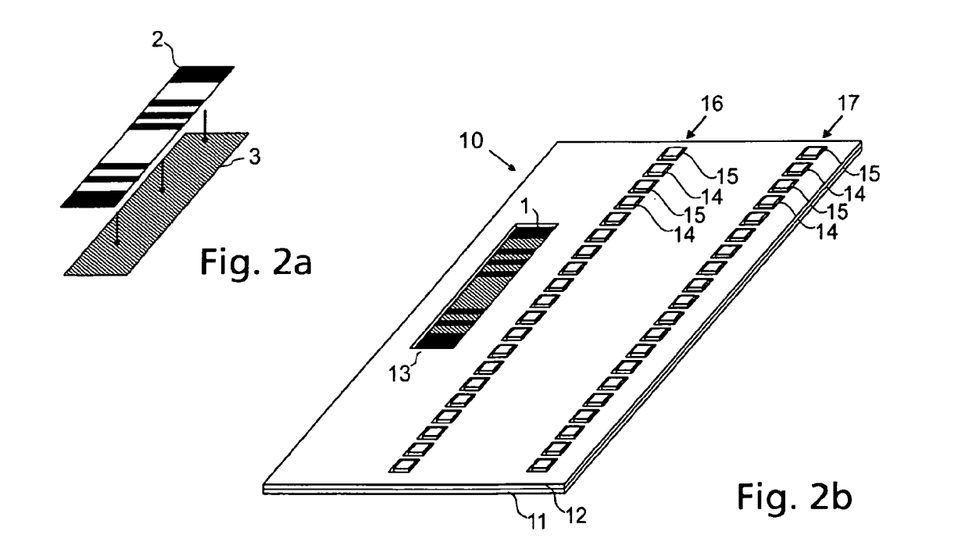
Figure 2C:
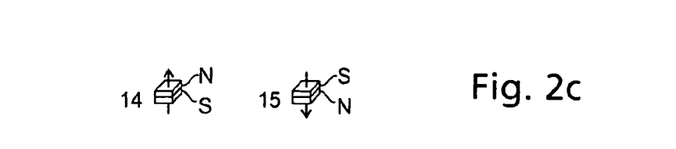

FIG. 2b shows a detail view of a calibration medium 10 which is equipped with a calibration sample 3 on which a bar code 2 is superimposed. The bar code 2 has been applied e.g. on a transparent foil and is affixed to a calibration sample 3 to guarantee their fixed mutual association, cf. FIG. 2a. The calibration sample 3 equipped with the bar code 2 is so clamped in between the two plates 11, 12 of the calibration medium that it is visible through a gap 13 of the upper plate 12. Further gaps of the upper plate 12 have a multiplicity of magnets 14, 15 inserted thereinto. The magnets are secured by the magnetic interaction with the lower plate 11, which for this purpose is magnetic. The upper plate 12 is non-magnetic. Alternatively, the magnets 14, 15 can of course also be fastened differently, e.g. by bonding or clamping. The magnets 14 and 15 are present in two parallel rows 16, 17 within which a magnet 14 and a magnet 15 respectively alternate. The magnets 14 are arranged with their magnetic north poles upward, but the magnets 15 conversely, with their magnetic south poles upward, cf. FIG. 2c.

In the transparent portions of the bar code 2 (bar code interstices) in which the calibration sample 3 is visible, the checking unit detects a multiplicity of calibration measurement values when scanning the calibration sample 3. The calibration measurement values are e.g. optical measurement values of the calibration sample which are employed for calibrating the checking unit. Upon scanning of the calibration medium, the bar code provides a modulation of the measurement values detected by the checking unit, because the bar code stripes are light-absorbing. This modulation is decoded by the checking unit in order to establish one or several target values required for calibration which are associated with the calibration sample 3.

Figure 3A:
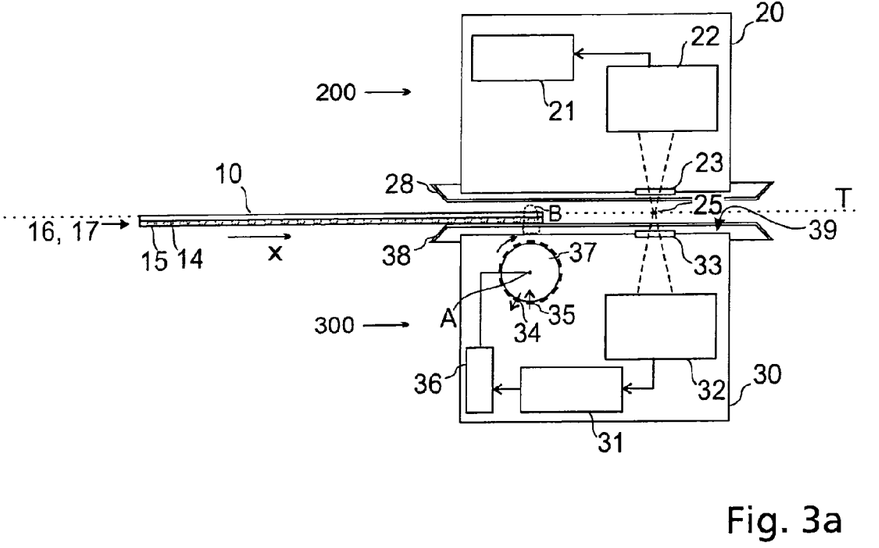

FIG. 3a represents the two checking units 200, 300 in a side view, with the side wall of the housings 20, 30 facing the viewer being respectively omitted in FIG. 3a for the representation. In this example, only the checking unit 300 is a checking unit according to the invention. The checking unit 200 is advantageous for enabling a double-sided scanning of the material web, but not necessary with regard to the invention. In the checking unit 200 there can be provided a control device 21 which controls the detecting of measurement values by the measurement elements 22. To prevent an inadvertent false insertion of the calibration medium 10, however, the checking unit 200 has no drive means according to the invention. For the calibration medium 10 can then be captured by the drive means of the checking unit 300 only in the shown orientation when the (dashed) magnets 14, 15 point downward, cf. FIG. 3a. The checking unit 200 detects with the aid of its measurement elements 22 (shown only schematically) measurement values from the upper side of the calibration sample 3 of the calibration medium 10. The calibration sample 3 can be equipped on its upper side with a further bar code which generally differs from the bar code 2 on its underside which is detected by the checking unit 300, in order to likewise feed a target value to the checking unit 200 for its calibration. The further bar code is provided e.g. by a further foil which is affixed to the upper side of the calibration sample.

Figure 3B:
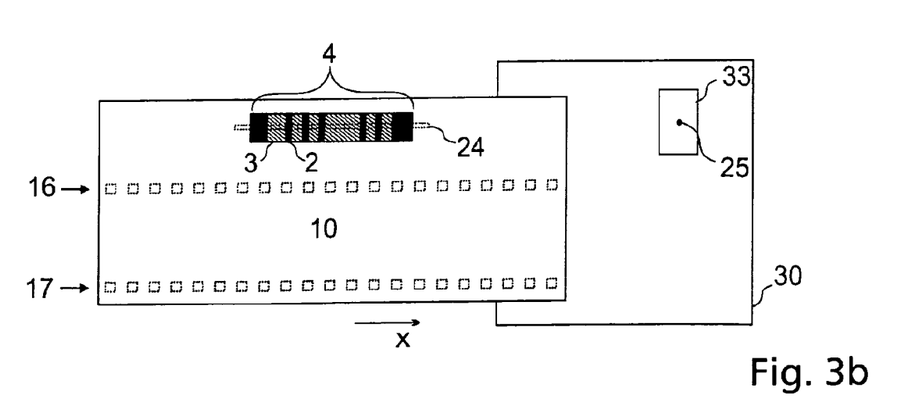

The checking unit 300 has a housing 30 having encapsulated therein both the measurement elements 32 (shown only schematically) and the drive means 34, 35, 37 for transporting the calibration medium 10. The housing 30 is completely shut off in order to keep soiling and moisture from the environment away from the drive means and from the measurement elements 32 of the checking unit 300. A control device 31 controls the measurement elements 32 and processes the detected measurement values. The control device 31 has set up therein operating modes for detecting the material web and for calibrating the checking unit 300 (and, where applicable, the checking unit 200). The measurement elements 32 are, in this example, configured for checking optical properties of the material web and detect the measurement values of the material web or of the calibration medium at the detection site 25 through a window 33 which is present on the side 39 of the housing 30 facing the transport plane T. In the case of optical measurement elements 32, these comprise e.g. at least one light source and a detector. FIG. 3b shows a plan view of the checking unit 300 according to the invention from FIG. 3a. Motion of the calibration medium 10 along the transport direction x causes the measurement portion 24 of the calibration medium to move through the detection site 25, whereby the measurement elements 32 detect a multiplicity of measurement values of the measurement portion 24.

The control device 31 moreover controls the motor 36 by which the drive wheel 37 can be set rotating around the rotational axis A. The rotation of the drive wheel 37 causes the magnets 34, 35 which are arranged alternately along the circumference of the drive wheel 37 to move. The magnets 34 are arranged such that their magnetic north poles point radially outward, but the magnets 35 such that their magnetic south poles point radially outward. The rotation of the drive wheel 37 causes the magnetic force of the magnets 34 and of the magnets 35 to act alternately in the capture region B of the drive means, cf. FIG. 3a.

For calibration, the rotation of the drive wheel 37 is first started and the calibration medium 10 subsequently inserted between the two checking units 200, 300 until one of its magnets 14, 15 passes into the capture region B of the magnets 34, 35 of the drive wheel. As soon as the rotation of the drive wheel 37 causes one of the magnets 34 of the drive wheel to pass into direct proximity of the housing side 39, its magnetic force acts in the capture region B attractively on the first magnet 15 of the inserted calibration medium 10 (position shown in FIG. 3a). The attractive magnetic interaction between the magnets 15 and 34 causes the calibration medium 10 to move along the transport direction x in synchronism with the rotation of the drive wheel 37. The feed force transporting the calibration medium past the checking unit 300 is produced alternately by the attractive magnetic interaction between the magnets 14 and 35 and the attractive magnetic interaction between the magnets 15 and 34. The guide element 38 acts in so doing as a spacer for the calibration medium 10 in order for the calibration medium 10 not to move toward the housing side 39. As soon as the last magnet of the calibration medium has passed the capture region B, there is no longer any feed force acting on the calibration medium 10.

Figure 4A:
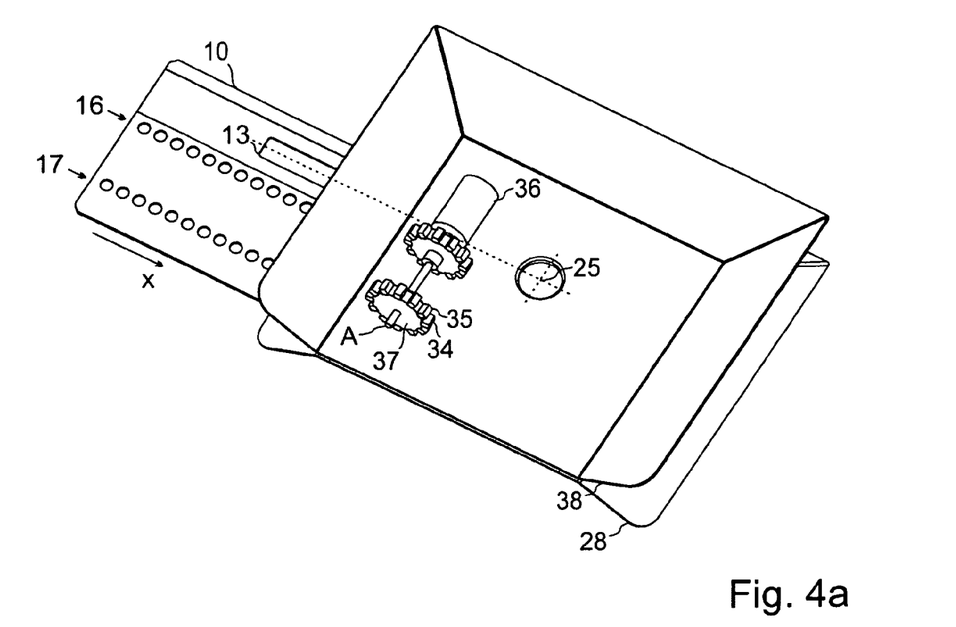
Figure 4B:
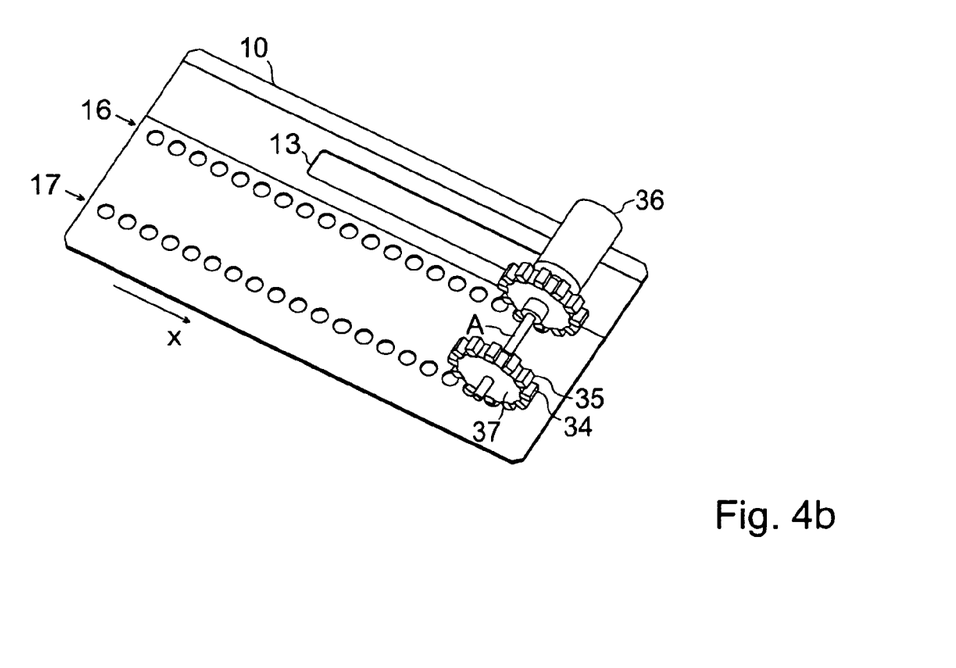

FIG. 4a shows a first embodiment of the drive means as they are employable for the example of FIGS. 3a and 3b. The drive means 34, 35, 37 and the motor 36 are all arranged in the housing of the checking unit, the calibration medium 10 outside. In the representation, the housing of the checking unit and the remaining constituents of the checking unit are omitted, however, with only the guide elements 28, 38 being shown. The guide element 38 has an opening through which the measurement elements of the checking unit are directed onto the detection site 25. As drive means there are employed in this example two drive wheels 37 offset transversely to the transport direction, which are fastened to the same rotational axis A and driven by the motor 36. Along their circumference the magnets 34, 35 are arranged with alternate magnetic polarity, as described above. The magnets 34, 35 of the two drive wheels 37 are arranged congruently with each other along the circumference with their magnetic polarity. In the calibration medium 10 the positions of the magnets 14, 15 along the two rows 16, 17 are shown only schematically in FIGS. 4a, 4b, and the calibration sample to be arranged in the gap 13 is omitted. FIG. 4b shows the arrangement from FIG. 4a without the guide elements 38, 28.

Figure 5:
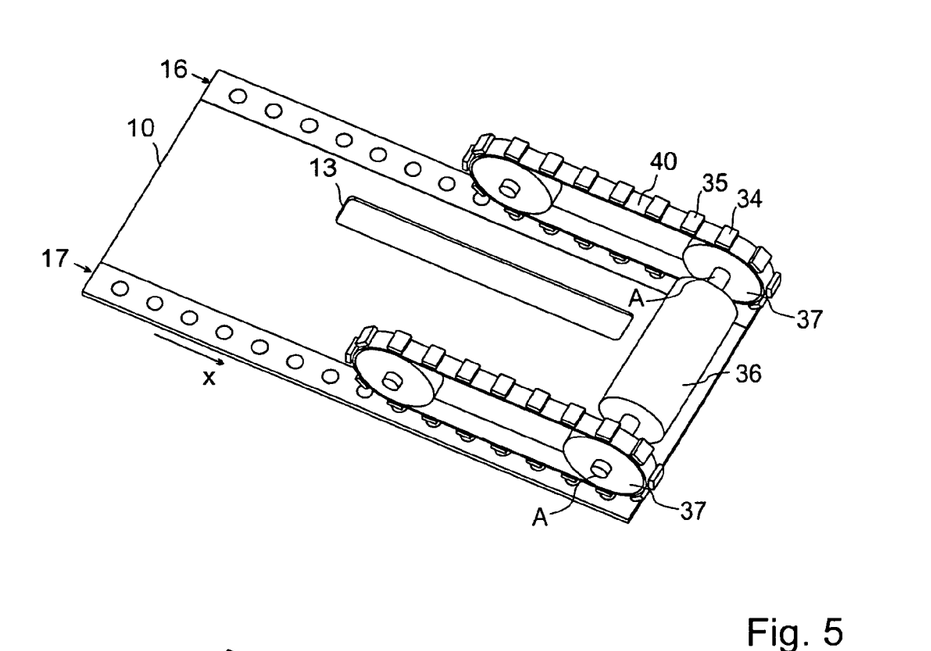

FIG. 5 shows a second exemplary embodiment of the drive means according to the invention. The drive means 34, 35, 37, 40 and the motor 36 are all arranged in the housing of the checking unit, the calibration medium 10 outside. The motor 36 drives via its rotational axis A two drive wheels 37 which are mutually offset transversely to the transport direction x. Both drive wheels are respectively connected via a belt 40 to a further drive wheel offset along the transport direction, in order to drive it as well. The two belts 40 respectively have arranged thereon magnets 34, 35 with alternate magnetic polarity. The calibration medium 10, in this exemplary embodiment, is moved along the transport direction x at the onset of transport only through the interaction with two magnets, but in the course of being transported past it is moved with all magnets that are arranged on the side of the belt facing the calibration medium 10.

Figure 6:
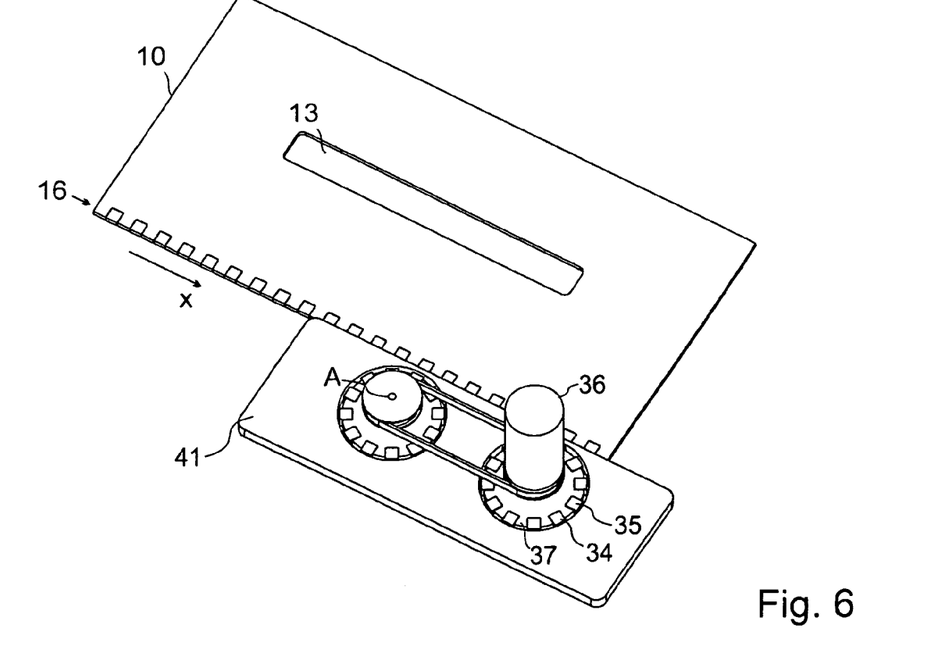

FIG. 6 represents a third exemplary embodiment of the drive means according to the invention. The drive means 34, 35, 37 and the motor 36 are all arranged in the housing of the checking unit, the calibration medium 10 outside. The motor 36 drives the drive wheel 37, which also drives a second drive wheel through coupling by means of a belt. As in the example of FIGS. 3 and 4, these drive wheels 37 also have arranged alternately along the circumference magnets 34, 35 whose magnetic polarity points alternately radially outward and radially inward. In contrast to the previous examples, however, there are employed here drive wheels 37 whose rotational axis A is oriented perpendicularly to the transport plane T of the calibration medium 10. The two drive wheels are inserted into corresponding depressions of a plate 41 which is arranged within the housing of the checking unit or forms a part of the housing wall. Instead of the two drive wheels shown in FIG. 6, a single drive wheel 37 can also be employed. The drive means from FIG. 4 or those from FIG. 5 can also be employed analogously in the same orientation, i.e. with the rotational axis A perpendicular to the transport plane T. With this orientation of the rotational axes A an edge of the calibration medium 10 is equipped with a row 16 of magnets 14, 15, in contrast to the calibration medium of FIGS. 2b and 3b, cf. FIG. 6. Thus, they can produce with the magnets 34, 35 of the drive wheels 37 a magnetic interaction of sufficient strength.

The invention claimed is:

1. A checking unit for checking a material web transportable past the checking unit along a transport direction, the checking unit comprising:
measurement elements configured for detecting measurement values of the material web transportable past the checking unit and for detecting measurement values of a calibration medium transportable past the checking unit along the transport direction;
an operating mode in which the checking unit can be calibrated with the aid of the calibration medium which is transportable past the checking unit along the transport direction for calibration;
one or more drive means configured for transporting the calibration medium past the checking unit through a contactless interaction;
a housing having arranged therein both the drive means for transporting the calibration medium past and the measurement elements for detecting the measurement values of the calibration medium.

2. The checking unit according to claim 1, wherein the drive means are encapsulated by the housing of the checking unit such that the drive means are protected from moisture and contaminants from the environment in which the checking unit is to be used.

3. The checking unit according to claim 1, wherein the checking unit has at least respectively two of the drive means arranged mutually offset transversely to the transport direction of the calibration medium and configured and arranged to interact with the calibration medium in mutual synchronism.

4. The checking unit according to claim 1, wherein the drive means arranged in the housing of the checking unit has several magnets through which a calibration medium having magnetic elements is transportable past the checking unit along the transport direction, the transporting past of the calibration medium being obtained through a magnetic interaction between the magnets of the drive means and the magnetic elements of the calibration medium.

5. The checking unit according to claim 4, wherein the magnets of the drive means are arranged in the housing of the checking unit such that the lateral position of the calibration medium that the latter assumes upon the transporting of the calibration medium past the checking unit is reproducible.

6. The checking unit according to claim 4, wherein the magnets of the drive means are arranged in the housing of the checking unit and configured that, while the calibration medium is being transported past the checking unit, an attractive interaction between the magnets of the drive means and the magnetic elements of the calibration medium is produced in order to obtain a lateral guidance of the calibration medium continuously upon the detecting of the measurement values of the calibration medium.

7. The checking unit according to claim 4, wherein the magnets of the drive means are movable through a motion of the drive means such that a calibration medium having magnetic elements and present in a capture region of the drive means is transportable past the checking unit through a magnetic interaction with the moved magnets of the drive means.

8. The checking unit according to claim 4, wherein mutually adjacent magnets of the drive means are arranged with the magnetic poles of the mutually adjacent magnets alternately oriented opposite to each other, so that, through the motion of the magnets of the drive means, the force of a magnetic north pole and of a magnetic south pole can be alternately provided in the capture region of the drive means.

9. The checking unit according to claim 4, wherein the drive means have at least one drive wheel through whose rotation the magnets of the drive means are movable.

10. The checking unit according to claim 9, wherein the rotational axis of the drive wheel is oriented parallel to the transport plane of the calibration medium and perpendicularly to the transport direction of the calibration medium.

11. The checking unit according of claim 9, wherein the rotational axis of the drive wheel is oriented perpendicularly to the transport plane of the calibration medium.

12. The checking unit according to claim 9, wherein the drive means have at least one drive wheel and a carrier element which is arranged at least in certain portions along the circumference of the drive wheel and is movable through the rotation of the drive wheel, the magnets being arranged on the carrier element on the side facing away from the drive wheel.

13. The checking unit according to claim 4, wherein the drive means have at least one drive wheel along whose circumference the magnets are arranged such that the magnetic field lines of the respective magnet point radially outward with regard to a rotational axis of the drive wheel.

14. The checking unit according to claim 13, wherein along the circumference of the drive wheel there are arranged several magnets whose magnetic north poles point radially outward and several magnets whose magnetic south poles point radially outward, with the magnets succeeding each other along the circumference of the drive wheel arranged such that the magnetic north poles and the magnetic south poles of the mutually adjacent magnets are alternately oriented radially outward.

15. A method for calibrating a checking unit wherein the checking unit is configured for checking a material web transportable past the checking unit along a transport direction and has a housing having arranged therein both drive means for transporting a calibration medium past and measurement elements for detecting measurement values of the material web and measurement values of the calibration medium, wherein the method comprises the steps of:
arranging a calibration medium on a side of the checking unit intended for sensing measurement values such that the calibration medium reaches the capture region of the drive means;
transporting the calibration medium past the checking unit along the transport direction with the aid of the drive means, with the calibration medium being transported past the checking unit through a contactless interaction with the drive means of the checking unit;
detecting a multiplicity of measurement values at different positions within a measurement portion of the calibration medium with the aid of the measurement elements of the checking unit while the calibration medium is being transported past the checking unit;
calibrating the checking unit with the aid of the detected measurement values of the calibration medium.

16. The method according to claim 15, wherein the calibration medium is only brought into the capture region of the drive means after a motion of the drive means has been started.

17. The method according to claim 15, wherein the calibration medium has several magnetic elements whose arrangement on the calibration medium is coordinated with the arrangement of magnets of the drive means of the checking unit such that the calibration medium, when the magnets of the drive means are moved, is transported past the checking unit in synchronism with a motion of the magnets of the drive means.

18. The method according to claim 15, wherein from the multiplicity of measurement values that are detected by a measurement portion of the calibration medium while the calibration medium is being transported past, both a multiplicity of calibration measurement values are established and at least one target value required for calibrating the checking unit is established.

19. The method according to claim 18, wherein there are present in the measurement portion of the calibration medium a calibration sample and a bar code superimposed on the calibration sample and representing at least one target value required for calibrating the checking unit.

20. The method according to claim 18, wherein the calibration sample respectively has a bar code on its side facing the checking unit and its side facing away from the checking unit, with the bar code facing the checking unit representing a target value required for calibrating the checking unit and the bar code facing away from the checking unit representing a target value required for calibrating a further checking unit which is arranged so as to oppose the checking unit.

* * * * *